(12) United States Patent
Brace et al.

(10) Patent No.: US 6,379,364 B1
(45) Date of Patent: Apr. 30, 2002

(54) DUAL DRILL GUIDE FOR A LOCKING BONE PLATE

(75) Inventors: Michael Brace, Lansdale; Roger Berger, Wayne; Hansjuerg W. Emch, Philadelphia, all of PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/560,897

(22) Filed: Apr. 28, 2000

(51) Int. Cl.$^7$ .............................................. A61B 17/90
(52) U.S. Cl. ............................................ 606/96; 606/86
(58) Field of Search ............................. 606/96, 69, 86, 606/98

(56) References Cited

U.S. PATENT DOCUMENTS

| | | | |
|---|---|---|---|
| 1,831,813 A | 11/1931 | Levedahl | |
| 2,200,120 A | 5/1940 | Nauth | 128/83 |
| 2,235,419 A | 3/1941 | Callahan et al. | 128/83 |
| 2,248,054 A | 7/1941 | Becker | 145/52 |
| 2,267,157 A | 12/1941 | Lippincott | 128/83 |
| 2,490,364 A | 12/1949 | Livingston | 128/92 |
| 2,494,229 A | 1/1950 | Collison | 128/92 |
| 2,500,370 A | 3/1950 | McKibbin | 128/92 |
| 2,839,953 A | 6/1958 | Hanger | 77/13 |
| 2,935,905 A | 5/1960 | Winslow | 77/55 |
| 3,244,170 A | 4/1966 | McElvenny | 128/92 |
| 3,530,860 A | 9/1970 | Majoros | 128/305 |
| 3,664,022 A | 5/1972 | Small | 32/2 |
| 3,704,707 A | 12/1972 | Halloran | 128/92 EB |
| 3,727,611 A | 4/1973 | Schultz | 128/92 EB |
| 3,760,802 A | 9/1973 | Fischer et al. | 128/92 BC |
| 3,765,034 A | 10/1973 | Johnston | 3/1 |
| 3,814,089 A | 6/1974 | Deyerle | 128/92 EB |
| 3,867,932 A | 2/1975 | Huene | 128/92 E |
| 3,892,232 A | 7/1975 | Neufeld | 128/92 EB |

(List continued on next page.)

FOREIGN PATENT DOCUMENTS

| | | |
|---|---|---|
| DE | 36 17 207 A1 | 11/1987 |
| DE | 41 09 440 A1 | 4/1992 |
| DE | 42 38 582 A1 | 5/1994 |
| DE | 198 28 137 A1 | 1/2000 |
| EP | 0 153 831 A2 | 9/1985 |
| EP | 0 201 011 A2 | 11/1986 |
| EP | 0 240 004 A2 | 10/1987 |
| EP | 0 307 241 A2 | 3/1989 |
| EP | 0 460 447 A1 | 12/1991 |
| EP | 0 495 488 A2 | 7/1992 |
| EP | 0 518 071 A1 | 12/1992 |
| EP | 0 633 748 B1 | 3/1998 |
| EP | 0 880 938 A1 | 12/1998 |
| EP | 0 683 651 B1 | 9/1999 |
| FR | 2 700 462 | 7/1994 |
| FR | 2 718 014 | 10/1995 |
| GB | 2 243 316 A | 10/1991 |
| JP | 9075366 | 3/1997 |
| WO | WO 94/15556 | 7/1994 |
| WO | WO 98/34569 | 8/1998 |
| WO | WO 99/59481 | 11/1999 |

OTHER PUBLICATIONS

*Synthes Maxilofacial*, catalog, 9/97, pp. 3–9, 3–30, 3–33, 3–34, 3–35, 3–40, and 4–27.
*Synthes Spine*, catalog, 1/98, pp. 1–3, 1–46, 1–70, 1–71, 3–2, 3–6, 3–18, 3–19, and 3–21.

(List continued on next page.)

*Primary Examiner*—Jeffrey A. Smith
*Assistant Examiner*—Michael B. Priddy
(74) *Attorney, Agent, or Firm*—Pennie & Edmonds LLP

(57) ABSTRACT

A surgical drill guide assembly for demountable attachment to the fastener holes of a bone plate is provided. The drill guide assembly includes a pair of alignment drill tubes that are aligned with corresponding fastener holes in the bone plate, and a pair of expandable bushings that are configured and dimensioned to engage the fastener holes. The surgical drill guide assembly is releasably lockable to the bone plate.

12 Claims, 8 Drawing Sheets

U.S. PATENT DOCUMENTS

| | | |
|---|---|---|
| 3,895,444 A | 7/1975 | Small ................... 32/10 A |
| 4,119,092 A | 10/1978 | Gil ....................... 128/92 D |
| 4,251,216 A | 2/1981 | Weissman .............. 433/215 |
| 4,253,784 A | 3/1981 | Anderson ........... 408/115 R |
| 4,312,337 A | 1/1982 | Donohue ............. 128/92 EB |
| 4,325,373 A | 4/1982 | Silvenko et al. ....... 128/303 R |
| 4,341,206 A | 7/1982 | Perrett et al. ........ 128/92 EB |
| 4,360,012 A | 11/1982 | McHarrie et al. ..... 128/92 EB |
| 4,383,527 A | 5/1983 | Asnis et al. .......... 128/92 EB |
| 4,399,813 A | 8/1983 | Barber ................. 128/92 EC |
| 4,409,973 A | 10/1983 | Neufeld ................. 128/92 E |
| 4,450,835 A | 5/1984 | Asnis et al. .......... 128/92 EB |
| 4,465,065 A | 8/1984 | Gotfried .............. 128/92 BB |
| 4,502,475 A | 3/1985 | Weigle et al. ........ 128/92 EB |
| 4,522,201 A | 6/1985 | Tongue ................. 128/92 EB |
| 4,528,980 A | 7/1985 | Kenna .................. 128/92 EB |
| 4,537,185 A | 8/1985 | Stednitz ................. 128/92 B |
| 4,541,424 A | 9/1985 | Grosse et al. ......... 128/92 EB |
| 4,549,538 A | 10/1985 | Schadrack, III et al. ................... 128/92 EB |
| 4,570,624 A | 2/1986 | Wu ....................... 128/92 EB |
| 4,586,497 A | 5/1986 | Dapra et al. ........... 128/92 E |
| 4,599,999 A | 7/1986 | Klaue .................... 128/92 EB |
| 4,608,972 A | 9/1986 | Small .................... 128/92 EB |
| 4,612,922 A | 9/1986 | Barber .................. 128/92 EB |
| 4,686,972 A | 8/1987 | Kurland ................. 128/92 V |
| 4,708,139 A | 11/1987 | Dunbar, IV ........... 128/305.1 |
| 4,713,077 A | 12/1987 | Small ...................... 623/16 |
| 4,714,469 A | 12/1987 | Kenna ..................... 623/17 |
| 4,716,893 A | 1/1988 | Fischer et al. ........ 128/92 YF |
| 4,733,654 A | 3/1988 | Marino ................. 128/92 YY |
| 4,738,255 A | 4/1988 | Goble et al. .......... 128/92 YF |
| 4,744,353 A | 5/1988 | McFarland ........... 128/92 VD |
| 4,747,400 A | 5/1988 | Koeneman et al. ..... 128/95 Z |
| 4,760,843 A | 8/1988 | Fischer et al. ........ 128/92 YF |
| 4,787,377 A | 11/1988 | Laboureau ............ 128/92 VD |
| 4,788,970 A | 12/1988 | Kara et al. ........... 128/92 ND |
| 4,798,213 A | 1/1989 | Doppelt ................... 128/754 |
| 4,813,407 A | 3/1989 | Vogen ........................ 128/92 |
| 4,823,780 A | 4/1989 | Odnesten et al. ..... 128/92 VD |
| 4,834,080 A | 5/1989 | Brown .................. 128/92 VP |
| 4,848,327 A | 7/1989 | Perdue ................... 128/92 R |
| 4,852,558 A | 8/1989 | Outerbridge .......... 128/92 YF |
| 4,865,025 A | 9/1989 | Buzzi et al. ......... 128/92 VD |
| 4,881,535 A | 11/1989 | Sohngen ................... 606/98 |
| 4,903,691 A | 2/1990 | Heinl ......................... 128/92 |
| 4,907,577 A | 3/1990 | Wu ............................ 606/87 |
| 4,911,153 A | 3/1990 | Border ....................... 606/98 |
| 4,917,604 A | 4/1990 | Small ......................... 433/174 |
| 4,978,351 A | 12/1990 | Rozas ........................ 606/98 |
| 5,002,547 A | 3/1991 | Poggie et al. .............. 606/88 |
| 5,026,373 A | 6/1991 | Ray et al. .................. 606/61 |
| 5,026,375 A | 6/1991 | Linovitz et al. ............ 606/79 |
| 5,026,376 A | 6/1991 | Greenberg .................. 606/96 |
| 5,030,219 A | 7/1991 | Matsen, III et al. ........ 606/53 |
| 5,047,034 A | 9/1991 | Sohngen .................... 606/87 |
| 5,112,336 A | 5/1992 | Krevolin et al. ........... 606/96 |
| 5,112,337 A | 5/1992 | Paulos et al. .............. 606/96 |
| 5,133,720 A | 7/1992 | Greenberg .................. 606/96 |
| 5,139,520 A | 8/1992 | Rosenberg .................. 623/13 |
| 5,141,513 A | 8/1992 | Fortune et al. ............. 606/96 |
| 5,147,367 A | 9/1992 | Ellis ........................... 606/96 |
| 5,151,103 A | 9/1992 | Tepic et al. ................ 606/69 |
| 5,154,721 A | 10/1992 | Perez ......................... 606/117 |
| 5,176,681 A | 1/1993 | Lawes et al. ............... 606/64 |
| 5,180,384 A | 1/1993 | Mikhail ..................... 606/80 |
| 5,180,388 A | 1/1993 | DiCarlo ..................... 623/16 |
| 5,207,682 A | 5/1993 | Cripe ......................... 606/96 |
| 5,207,753 A * | 5/1993 | Badrinath ................... 606/96 |
| 5,250,055 A | 10/1993 | Moore et al. ............. 606/148 |
| 5,306,278 A | 4/1994 | Dahl et al. .................. 606/96 |
| 5,320,626 A | 6/1994 | Schmieding ................ 606/96 |
| 5,324,295 A | 6/1994 | Shapiro ...................... 606/86 |
| 5,346,496 A | 9/1994 | Pennig ....................... 606/96 |
| 5,350,380 A | 9/1994 | Goble et al. ............... 606/80 |
| 5,354,300 A | 10/1994 | Goble et al. ............... 606/80 |
| 5,364,399 A | 11/1994 | Lowery et al. ............. 606/69 |
| 5,366,457 A | 11/1994 | McGuire et al. ........... 606/86 |
| 5,403,322 A | 4/1995 | Herzenberg et al. ....... 606/98 |
| 5,409,329 A | 4/1995 | Juang ...................... 408/115 R |
| 5,409,493 A | 4/1995 | Greenberg .................. 606/96 |
| 5,423,826 A | 6/1995 | Coates et al. ............... 606/96 |
| 5,425,490 A | 6/1995 | Goble et al. ............... 227/175 |
| 5,429,641 A | 7/1995 | Gotfried ..................... 606/67 |
| 5,437,677 A | 8/1995 | Shearer et al. ............. 606/96 |
| 5,458,602 A | 10/1995 | Goble et al. ............... 606/96 |
| 5,462,549 A | 10/1995 | Glock ......................... 606/86 |
| 5,474,559 A | 12/1995 | Bertin et al. ............... 606/89 |
| 5,478,341 A | 12/1995 | Cook et al. ................. 606/62 |
| 5,489,210 A | 2/1996 | Hanosh ...................... 433/173 |
| 5,507,801 A | 4/1996 | Gisin et al. ................. 606/86 |
| 5,514,144 A | 5/1996 | Bolton ....................... 606/96 |
| 5,520,690 A | 5/1996 | Errico et al. ............... 606/61 |
| 5,531,746 A | 7/1996 | Errico et al. ............... 606/61 |
| 5,531,751 A | 7/1996 | Schultheiss et al. ....... 606/96 |
| 5,562,735 A | 10/1996 | Margulies ................... 623/17 |
| 5,584,838 A | 12/1996 | Rona et al. ................. 606/96 |
| 5,584,839 A | 12/1996 | Gieringer ................... 606/96 |
| 5,601,550 A | 2/1997 | Esser ......................... 606/54 |
| 5,613,970 A | 3/1997 | Houston et al. ............ 606/88 |
| 5,620,449 A | 4/1997 | Faccioli et al. ............ 606/98 |
| 5,632,747 A | 5/1997 | Scarborough et al. ..... 606/79 |
| 5,634,927 A | 6/1997 | Houston et al. ............ 606/96 |
| 5,637,112 A | 6/1997 | Moore et al. .............. 606/148 |
| 5,641,287 A | 6/1997 | Gittleman ................... 433/75 |
| 5,643,274 A | 7/1997 | Sander et al. .............. 606/104 |
| 5,649,930 A | 7/1997 | Kertzner ..................... 606/96 |
| 5,665,086 A | 9/1997 | Itoman et al. .............. 606/64 |
| 5,669,915 A | 9/1997 | Caspar et al. .............. 606/96 |
| 5,676,666 A | 10/1997 | Oxland et al. .............. 606/61 |
| 5,676,667 A | 10/1997 | Hausman .................... 606/69 |
| 5,683,400 A | 11/1997 | McGuire .................... 606/96 |
| 5,697,933 A | 12/1997 | Gundiapalli et al. ....... 606/96 |
| 5,700,265 A * | 12/1997 | Romano ..................... 606/80 |
| 5,713,905 A | 2/1998 | Goble et al. ............... 606/80 |
| 5,725,532 A | 3/1998 | Shoemaker .................. 606/96 |
| 5,743,916 A | 4/1998 | Greenberg et al. ......... 606/102 |
| 5,746,743 A | 5/1998 | Greenberg .................. 606/96 |
| 5,755,721 A | 5/1998 | Hearn ......................... 606/96 |
| 5,766,179 A | 6/1998 | Faccioli et al. ............. 606/98 |
| 5,769,856 A | 6/1998 | Dong et al. ................. 606/96 |
| 5,800,551 A | 9/1998 | Williamson et al. ........ 606/19 |
| 5,817,098 A | 10/1998 | Albrektsson et al. ....... 606/96 |
| 5,833,693 A | 11/1998 | Abrahami ................... 606/96 |
| 5,836,950 A | 11/1998 | Hansson ..................... 606/65 |
| RE36,020 E | 12/1998 | Moore et al. .............. 606/144 |
| 5,851,207 A | 12/1998 | Cesarone .................... 606/69 |
| 5,860,980 A | 1/1999 | Axelson, Jr. et al. ....... 606/88 |
| 5,885,300 A | 3/1999 | Tokuhashi et al. .......... 606/99 |
| 5,888,034 A | 3/1999 | Greenberg ................ 408/115 R |
| 5,891,150 A | 4/1999 | Chen .......................... 606/96 |
| 5,895,389 A | 4/1999 | Schenk et al. .............. 606/96 |
| 5,899,908 A | 5/1999 | Kuslich et al. ............. 606/96 |
| 5,904,685 A | 5/1999 | Walawalkar ................ 606/73 |
| 5,910,143 A | 6/1999 | Cripe et al. ................ 606/87 |
| 5,935,128 A | 8/1999 | Carter et al. ................ 606/69 |
| 5,938,686 A | 8/1999 | Benderev et al. .......... 606/232 |
| 5,951,561 A | 9/1999 | Pepper et al. .............. 606/80 |
| 5,954,722 A | 9/1999 | Bono ......................... 606/61 |
| 5,954,769 A | 9/1999 | Rosenlicht .................. 623/16 |
| 5,961,530 A | 10/1999 | Moore et al. .............. 606/148 |

| | | |
|---|---|---|
| 6,007,535 A | 12/1999 | Rayhack et al. .............. 606/57 |
| 6,010,509 A | 1/2000 | Delgado et al. .............. 606/88 |
| 6,013,083 A | 1/2000 | Bennett ...................... 606/104 |
| 6,033,409 A | 3/2000 | Allotta ........................ 606/80 |
| 6,036,695 A | 3/2000 | Smith .......................... 606/79 |
| 6,059,789 A | 5/2000 | Dinger et al. ................. 606/96 |
| 6,066,142 A | 5/2000 | Serbousek et al. ............ 606/96 |
| 6,079,681 A | 6/2000 | Stern et al. .............. 248/278.1 |
| 6,210,415 B1 | 4/2001 | Bester ......................... 606/96 |
| 6,235,034 B1 | 5/2001 | Bray .......................... 606/71 |

OTHER PUBLICATIONS

*Synthes* catalog, 3/97, pp. 3–15, 3–16, 3–17, 3–18, 3–19, 3–30, 3–31, 3–38, 3–83, 3–89, and 3–90.

*Stryker Implants*; Equinox Cervical Compression & Monobloc Anterior Plate System, undated.

*Stryker Implants*; Equinox Cervical Compression & Monobloc Anterior Plate System: Surgical Technique, undated.

Blackstone Medical Inc., Blackstone Anterior Cervical Plate, undated.

*Synthes Spine* Cervical Spine Locking Plate System: The Standard, 1995.

*Synthes Spine* Cervical Spine Lockign Plate System: New Additions, 1995.

*Synthes Spin* Cervical Spine Locking Plate, 1991.

\* cited by examiner

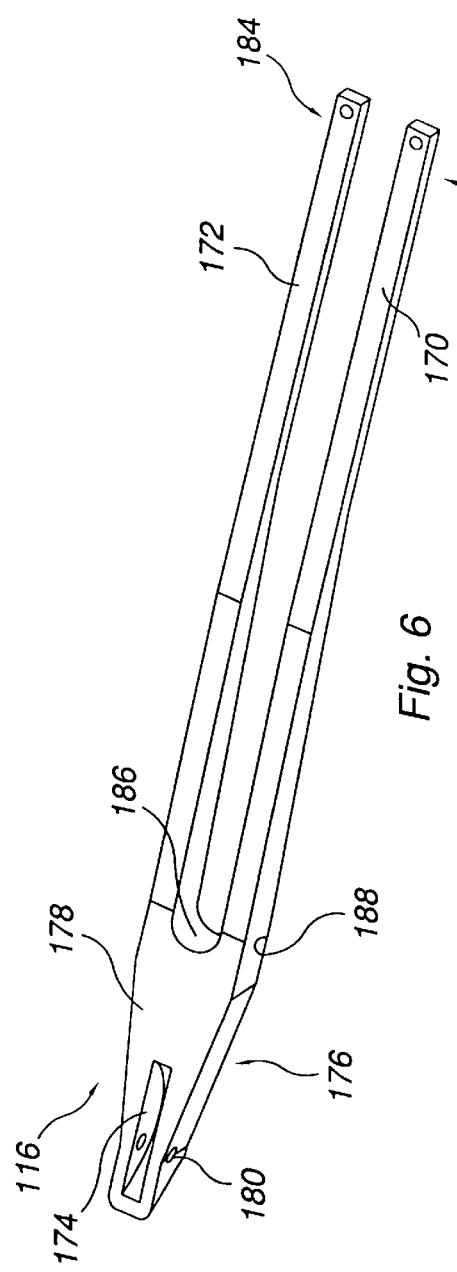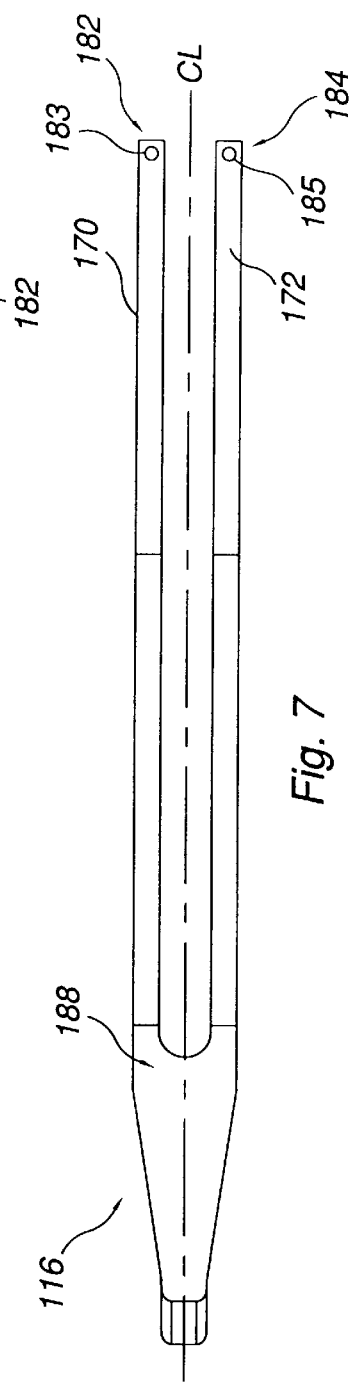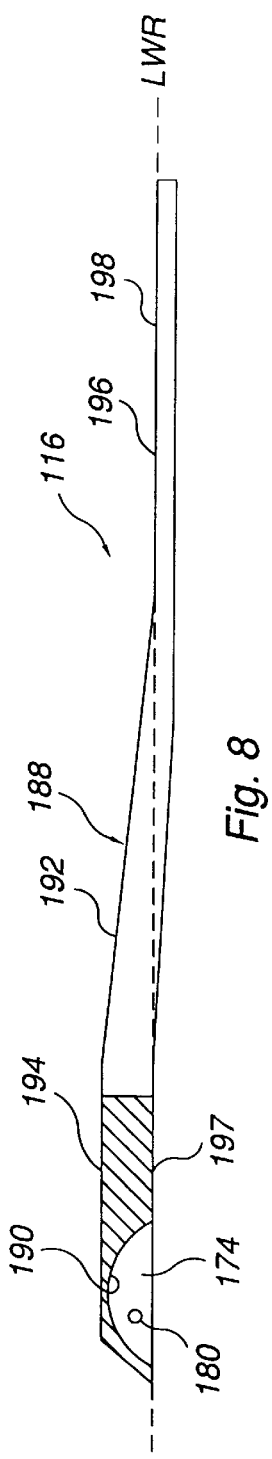

DUAL DRILL GUIDE FOR A LOCKING BONE PLATE

FIELD OF THE INVENTION

The present invention relates to a surgical drill guide and locking bone plate that are demountably attachable to each other for retaining a precise alignment therebetween. More particularly, the present invention relates to a surgical drill guide assembly with a plurality of alignment drill tubes each having an expandable bushing that engages a fastener hole in a locking bone plate.

BACKGROUND OF THE INVENTION

The use of surgical fixation plates for a variety of orthopedic applications is widely accepted. The plates are used by surgeons to mend, align, and alter compression of patient's bones, and are typically fastened to the bones with a plurality of fasteners such as screws that are installed through holes in the plate. Proper orientation and alignment of fasteners and secure surgical fixation of the plates is crucial to avoiding future complications after implantation.

Locking bone plates used in spinal applications, such as those sold by SYNTHES Spine, must be installed with special care, as the plates are used for long term, intravertebral fixation, bone-fragment fixation, and anterior decompression in the cervical region of the spine. The margin for error in spinal surgery is quite small, particularly because of the sensitivity of the spinal cord and the risk inherent with invasive procedures around the spinal cord. In particular, the dimensions of vertebral bone available for setting fasteners are fairly constrained.

Each fixation plate hole should properly align with its associated screw so that each screw is seated correctly with the plate. Any misalignment of the screw within the plate hole risks tissue damage. In addition, improperly seated screws may result in an unstable or insecure connection of the plate to the bony material, thus potentially defeating the usefulness of the plate. Locking plates, in particular, demand precise fastener alignment. Typical cervical locking plates are generally about 2–3 mm thick, and include screw holes that are inclined by 9° to 15° with respect to the surface of the plate for optimal screw placement in the cervical region of the spine. A variety of types of bone screws are available for securing the plate to the desired anatomical site, such as the expansion-head screws disclosed in U.S. Pat. No. 4,484,570.

Known drill guides for locking plates, such as disclosed in U.S. Pat. No. 5,851,207, generally include a guide member for guiding a drill bit. A hollow collet is disposed coaxially with the guide member and has a radially expandable forward end with a neck. The neck is configured to press outwardly against an inner wall of a plate hole when the collet is in an expanded position, thereby securing the drill guide to the bone plate. An inconvenience associated with this drill guide is that it includes only one guide member, so the drill guide must be removed and reoriented within each bone plate hole for drilling successive holes in tissue.

The desirability of providing a drill guide that includes more than one guide tube has been recognized. For example, U.S. Pat. No. 5,180,388 discloses an applicator device with two guide tubes attached to a handle. A scale on the handle allows accurate determination of the movement of a drill inserted through the guide tubes and thus the depth of each hole. U.S. Pat. No. 4,714,469 shows another drill guide with an elongated arm having a distal end which is shaped to match the profile of a spinal implant for which the apparatus is to be used. Grooves in the drill guide are adapted to accommodate a drill bit, and linear markings are provided on the surface of the drill guide so that the correct depth for drilling is obtained. U.S. Pat. No. 5,112,336 shows a drill guide and template for use in orthopedic surgery, comprising a template and handle connected by a lockable universal joint. The template is provided with pins so that the template can be set into bone. The pins prevent the template from moving while bores are being made in the bone. Drill bores are provided in the template to conform to a selected prosthesis which the surgeon intends to implant. Despite these drill guide developments, none meets the demands of surgeons working with bone plates, as none attach to a bone plate.

U.S. Pat. No. 4,465,065 discloses an L-shaped surgical device for the connection of a fractured neck to the shaft of a femur by means of a pre-drilled connector plate. The tool has a grip and connector arm extending at right angles, and the tool and plate are interconnected by means of a long screw which passes through a longitudinal bore along the connector arm into a tapped hole in the top of the fixator plate. Two pins firmly attached to the connector arm also engage with corresponding holes in the upper part of the plate. Guide tubes extend through holes in the device to holes in the plate. The tool cannot be readily demountably attached to a plate, because the interconnection means are not quickly releasable.

U.S. Pat. No. 5,676,666 discloses a cervical plate holder/guide clamp that is a modified fixation forceps, and includes a handle, pivot joint, and blades. Each blade includes a guide head with opposing lips which attach to a plate. Guide cylinders are slidably positionable in each guide head and are pushed down to contact with the openings in the plate. The opposing lips contact the outer periphery of the plate.

U.S. Pat. No. 5,364,399 discloses an anterior cervical plating system. A drill and tap guide assembly is mounted on a fixation plate to provide a firm foundation for accurately drilling and tapping screw holes into the vertebra to be instrumented. The drill and tap guide assembly includes an assembly support which is engaged to the plate by way of a positioning screw and cross pins mounting the positioning screw to the guide body. A tap sleeve and drill guide can then be supported by the assembly support, which both thereby provide accurate positioning for a drill.

U.S. Pat. No. 5,423,826 discloses an anterior cervical plate holder/drill guide. The guide comprises two arms which pivot with respect to each other and a foot attached at the end of each arm. Each foot has a hook which is adapted to securely grasp a spinal plate and a pair of thru-holes. Each hole is aligned with a screw bore in a spinal plate when the guide assembly is engaged to the plate. A number of double-headed fixation pins hold the plate in position against the cervical spine during drilling and tapping. The hook on each foot of the guide attaches to a notch on each end of the plate.

The above-described patents disclose drill guides that do not engage the plate only within the plate fastener holes that receive the bone screws.

SUMMARY OF THE INVENTION

The invention relates to a surgical drill guide assembly comprising a pair of alignment drill tubes each configured to receive and guide a surgical drill bit; a pair of bushings configured to slidably receive the pair of alignment drill tubes, the bushings each having a radially expandable forward end configured to engage fastener holes in a bone plate; an actuation bar; a drill guide assembly handle coupled to the actuation bar; and a base coupled to the drill guide assembly handle. The alignment drill tubes are pivotably connected to the actuation bar. The bushings are configured and dimensioned to expand within the bone plate fastener holes to releasably lock the bushings to the bone plate, such that movement of the actuation bar toward the base urges the drill tubes into the bushings for expansion of the forward ends thus locking the bushings within the fastener holes of the bone plate. The bone plate may include at least two fastener holes.

Advantageously, the radially expandable forward end comprises a plurality of finger portions. The radially expandable forward end may be circular. Preferably, the radially expandable forward end comprises a shoulder, a neck, and an outwardly projecting rim disposed forward of the neck.

Each alignment drill tube has a drilling axis, and the drilling axes are coplanar and converge along a central plane forward of the radially expandable forward end of the bushings. In a preferred embodiment, each alignment drill tube is oriented at an angle of between about 5 and 22° with respect to the central axis.

If desired, a latch can be included for releasably maintaining the actuation bar in an actuated position. When the expandable forward end of the bushing is circular shaped, and the fastener holes in the bone plate each have inner walls that define a circular shape, the expandable forward end is freely insertable and extractable from the bone plate fastener holes in a contracted position and engages the fastener holes when in an expanded position.

In additional embodiments of the assembly, the drill guide assembly handle is comprised of a grip pivotably connected to a handle member, and the grip is resiliently biased away from the handle member by leaf springs. Preferably, in a first position, the leaf springs maintain the grip and handle member in a spaced relation, with the bushings in non-expanded configurations and the alignment drill tubes in retracted positions. Application of a force to the grip and handle member counteracts the bias of the leaf springs and urges the grip and handle member to a second position, while moving the actuation bar toward the base, and urging the alignment drill tubes into the bushings for expansion of the forward ends.

The bone plate fastener holes may each have a wall thickness defined as the distance between a free-side surface and a bone-side surface of the bone plate. The radially expandable forward end of the bushing may comprise a shoulder, a neck, and an outwardly projecting rim disposed forward of the neck. The neck and rim together may span a length that is slightly longer than the thickness of the bone plate fastener hole wall, and the rim may abut the bone-side surface of the plate.

BRIEF DESCRIPTION OF THE DRAWINGS

Preferred features of the present invention are disclosed in the accompanying drawings, wherein similar reference characters denote similar elements throughout the several views, and wherein:

FIG. 6 is a perspective view of the actuation bar of the present invention;

FIG. 7 is a top view of the actuation bar of FIG. 6;

FIG. 8 is a cross-sectional side view of the actuation bar of FIG. 6;

DETAILED DESCRIPTION OF THE PREFERRED EMBODIMENTS

Figure 1:
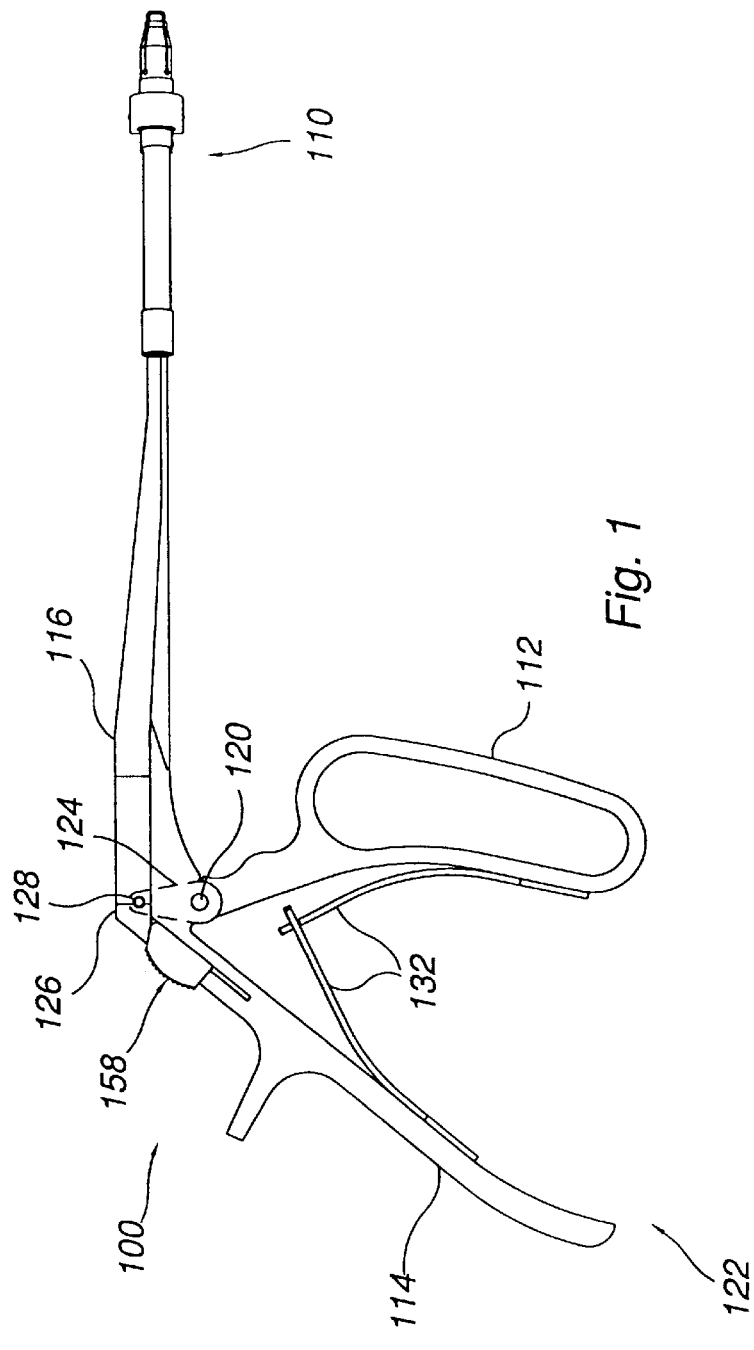
FIG. 1 is a side view of a surgical drill guide assembly in accordance with a preferred embodiment of the present invention.

Referring to FIG. 1, there is shown an exemplary surgical drill guide assembly 100, which is adapted for use with a cervical spine locking bone plate having a plurality of fastener holes. Assembly 100 includes an alignment device 110, grip 112, and handle member 114, along with actuation bar 116. Grip 112 and handle member 114 are pivotably connected by handle pin 120. Together, grip 112 and handle member 114 form a drill guide assembly handle 122, which allows a user to maneuver and use the drill guide assembly. In the preferred embodiment, handle 122 is located remotely from the drilling site, thereby leaving an open space near the locking bone plate. Grip 112 has an arm 124 that extends from handle pin 120 on grip 112 to pivotably attach to a first end 126 of actuation bar 116 at actuation pin 128. Preferably, leaf springs 132 are fastened to grip 112 and handle member 114 to bias the handle 122 toward a first or open position.

Figure 2:
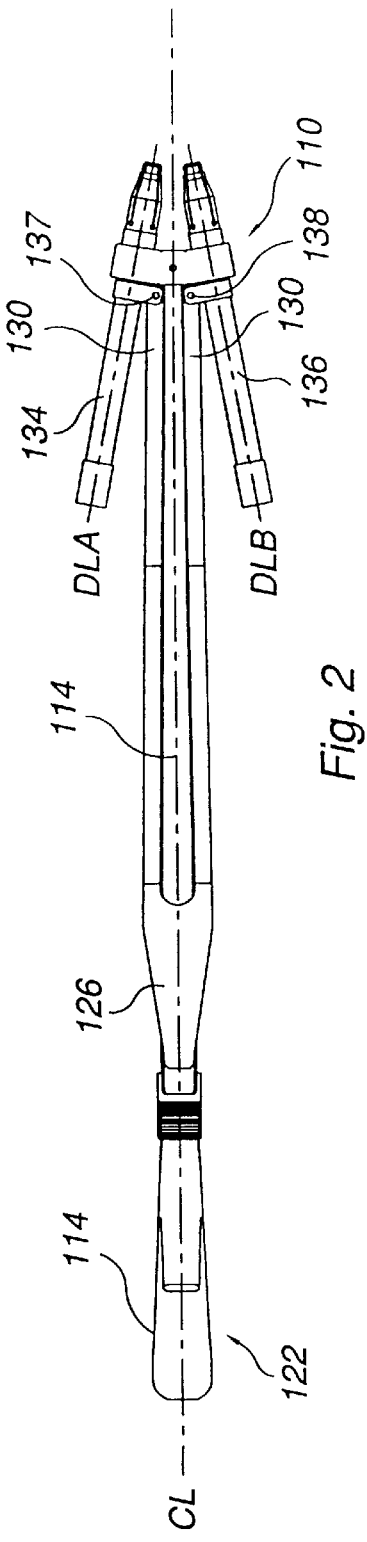
FIG. 2 is a top view of the surgical drill guide assembly of FIG. 1.

With reference to FIG. 2, drill guide assembly handle 122 and actuation bar 116 are disposed along a center plane that contains the center line CL and is perpendicular to the plane of the page. Preferably, alignment device 110 is substantially symmetrical about center plane. As will be discussed, alignment drill tubes 134, 136, which each may receive and direct the path of a drill bit, are aligned along drilling lines DLA and DLB respectively that converge forward of alignment device 110. Thus, the features of surgical drill guide assembly 100 permit the surgeon to make a lateral approach from either the left side or right side of the patient. A second end 130 of actuation bar 116 is pivotably attached with alignment device 110 at two points 137, 138.

Figure 3:
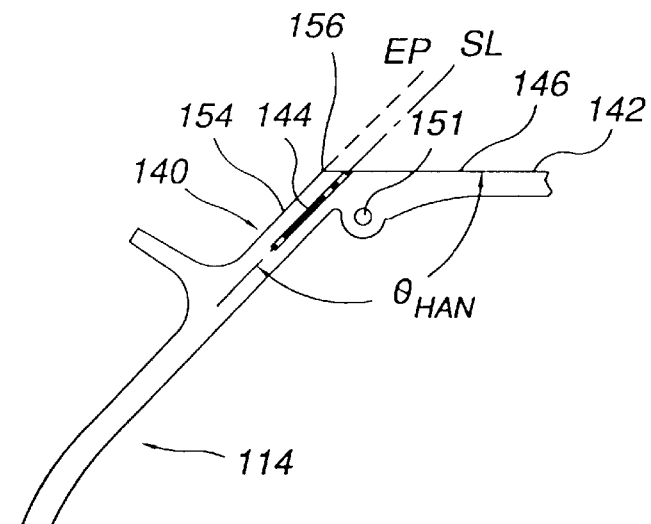
FIG. 3 is a side view of the handle member of the surgical drill guide assembly of FIG. 1.

As shown in FIG. 3, handle member 114 has two generally straight sections 140, 142. Section 140 has an upper slotted portion 144 that is disposed along line SL. Preferably, upper slotted portion 144 does not extend all the way through handle member 114. Instead, a second slotted portion is symmetrically disposed about the center plane on the opposite surface of handle member 114. Top surface 146 of section 142 and line SL defining an angle $\theta_{HAN}$. Preferably, angle $\theta_{HAN}$ is about 130° to optimally meet ergonomic considerations, although angles of between 90° and 150° can be used if desired. A hole 151 is provided to receive handle pin 120 for connecting grip 112 and handle member 114.

Figure 4:
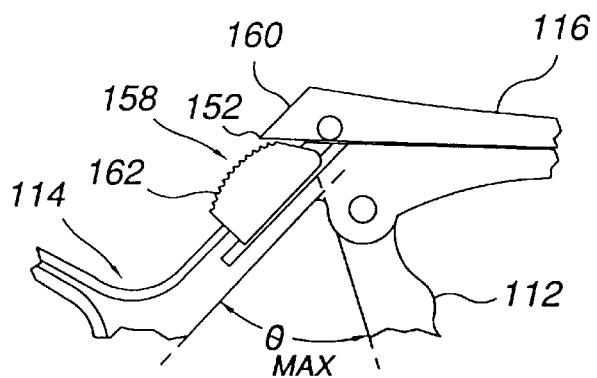
FIG. 4 is a partial side view of the handle of the present invention in the open position.

As shown in FIG. 4, drill guide assembly 100 is in the open position, with grip 112 at maximum separation angle $\theta_{MAX}$ from handle member 114. This open position also corresponds to an unlocked and unactuated state of actuation bar 116, in which vertex 152 of actuation bar 116 is located behind line EP that is generally parallel to line SL and defined along the outer edge 154 of section 140. Thus, in this open position, vertex 152 of actuation bar 116 is located behind vertex 156 of handle member 114, and latch 158 is in a lowered position and thus not engaged with actuation bar 116.

Figure 5:
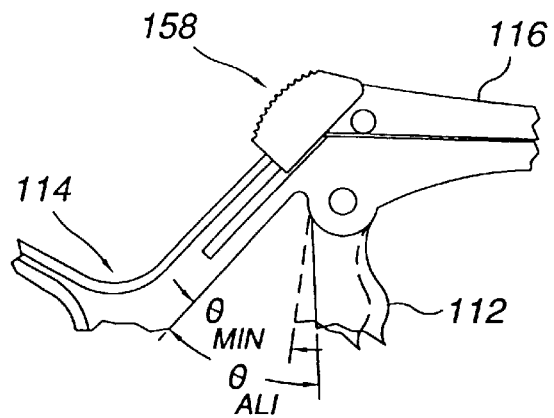
FIG. 5 is a partial side view of the handle of the present invention in the closed position.

When a surgeon squeezes grip 112 toward handle member 114, the arm 124 forces actuation bar 116 forward. As shown in FIG. 5, when grip 112 reaches a separation angle $\theta_{ALI}$ from handle member 114, drill guide assembly 100 is in a closed position with actuation bar 116 almost fully actuated. In this position, vertex 152 of actuation bar 116 is generally located along line EP such that side 160 of actuation bar 116 is generally co-linear with edge 154 of section 140.

As leaf springs 132 bias grip 112 and handle member 114 to an open position, a surgeon must continue to squeeze grip 112 and handle member 114 toward each other to maintain an actuated position of actuation bar 116. To facilitate use of surgical drill guide assembly 100, however, a latch 158 may be used to releasably lock actuation bar 116 in the almost fully actuated position with grip 112 separated by an angle $\theta_{ALI}$ from handle member 114. This obviates the need for a surgeon to continue to squeeze grip 112 and handle member 114 after proper actuation has occurred. Instead, the surgeon's thumb moves latch 158 into abutment with face 160 of actuation bar 116. Latch 158 remains in place due to the backward pressure applied by face 160 against it.

In a preferred embodiment, the movement of latch 158 is guided along slotted portions 144, with disengagement from slotted portions 144 prevented by an abutment on handle member 114. Alternatively, other means of restricting the travel of latch 158 may be used, such as a protrusion on face 160 of upper actuation bar 116. Preferably, latch 158 is also provided with teeth 162 or ridges to enhance tactile sensation between latch 158 and a surgeon's thumb, thereby facilitating movement of latch 158. Other latch means, such as pins or ratchet mechanisms, may also be used.

Actuation bar 116 is released from the locked position by squeezing grip 112 and handle member 114 to a slightly closer separation angle than $\theta_{ALI}$, such that grip 112 and handle member 114 are separated by an angle $\theta_{MIN}$. Because actuation bar 116 is moved away from latch 158 when separation angle $\theta_{MIN}$, is reached, the backward pressure applied by face 160 against latch 158 is diminished, and latch 158 is freely movable to a position that will not engage actuation bar 116.

Advantageously, a surgeon can operate drill guide 100 with only one hand, due to the ergonomic positioning of grip 112, handle member 114. In embodiments which include latch 115 for releasably locking grip 112 and handle member 114 with respect to each other, latch 158 is also ergonomically positioned so that one handed operation is still convenient.

Referring to FIGS. 6–8, actuation bar 116 is generally Y-shaped, and includes integrally formed first leg 170 and second leg 172. A channel 174 is formed at a proximal end 176 of actuation bar 116 in bottom side 178. The channel is configured and dimensioned to receive arm 124 of grip 112. Arm 124 is pivotably attached to actuation bar 116 with an actuation pin 128 that extends through a hole 180 coaxially located with a similarly sized thru-hole in arm 124. In addition, leg 170 has a distal end 182 with a hole 183. Similarly, leg 172 has a distal end 184 with a hole 185. Holes 183 and 185 extend from bottom side 178 to top side 188. The transition region 186 between legs 170, 172, including the surface defined between bottom side 178 and oppositely situated top side 188, is generally rounded. This minimizes stress concentration between legs 170, 172 when they are flexed. Referring to FIG. 8, actuation bar 116 is shown in cross-section taken along the center plane. Preferably, channel 174 has an arcuate upper surface 190. In addition, a stepped region 192 is provided between generally parallel regions 194 and 196 of each leg 170, 172. While bottom surface region 197 of actuation bar 116 is generally coplanar with top surface 146 of handle 122 about line LWR, stepped region 192 permits top surface region 198 of actuation bar 116 to also be generally coplanar with top surface 146 of handle 30 122 about line LWR. Such geometry of actuation bar 116 thus allows alignment device 110 to be smaller in size, thereby increasing the field of view of a surgeon using surgical drill guide assembly 100.

Figure 9:
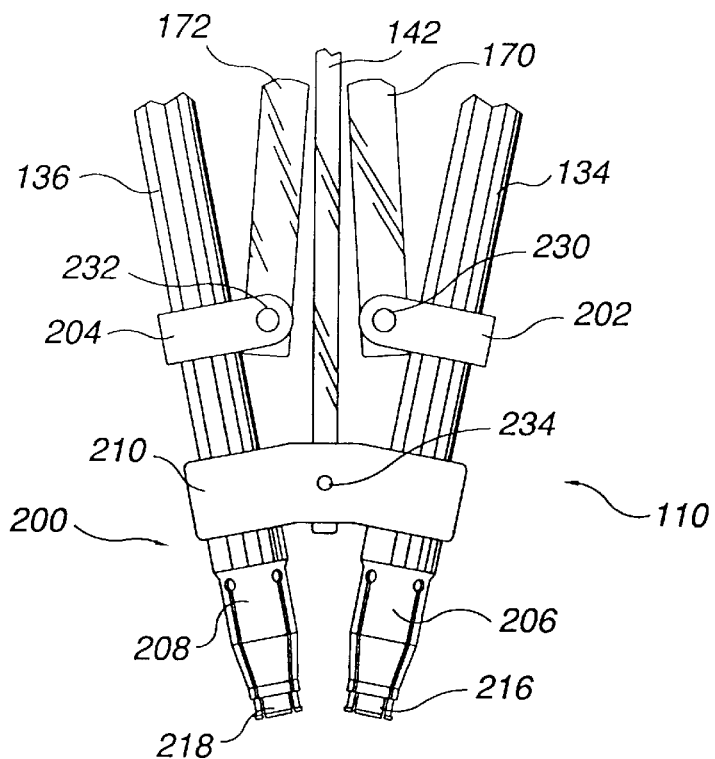
FIG. 9 is a partial top view of the alignment device of the present invention in the open position.
Figure 10:
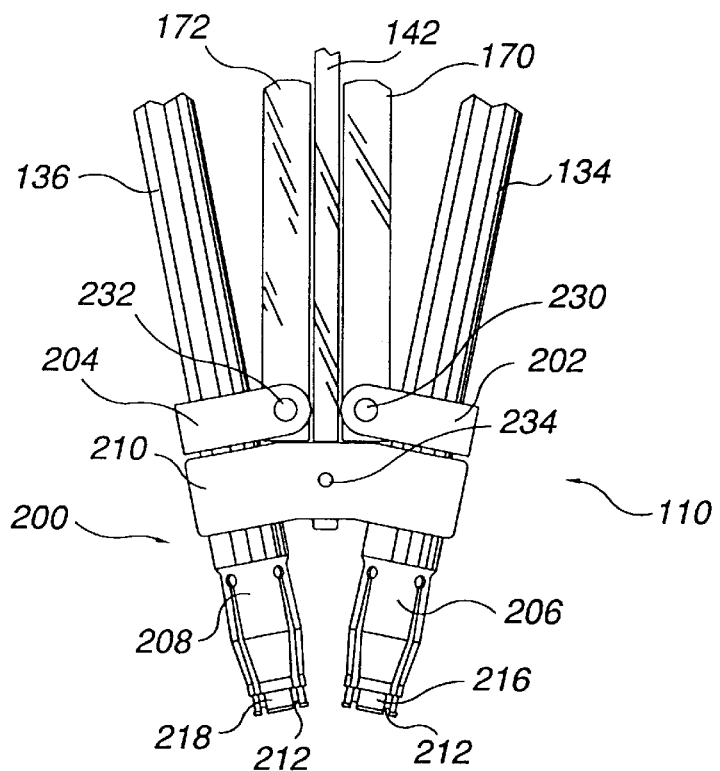
FIG. 10 is a partial top view of the alignment device of the present invention in the closed position.

Turning now to FIGS. 9 and 10, alignment device 110 includes alignment drill tubes 134, 136, bushing assembly 200, and bracket members 202, 204. Bushing assembly 200 includes bushings 206, 208 and base 210. Alignment device 110 is shown in FIG. 9 with alignment drill tubes 134, 136 in a retracted position, which may be achieved when grip 112 and handle member 114 are separated by an angle greater than $\theta_{ALI}$. When the surgeon squeezes handle 112, alignment drill tubes 134, 136 are moved forward within bushings 206, 208 respectively. As shown in FIG. 10, bushings 206, 208 reach an expanded position when front end 212 of alignment drill tube 134 reaches about front edge 216 of bushing 206, and when front end 214 of alignment drill tube 136 reaches about front edge 218 of bushing 208.

Bracket member 202 is fixed to alignment drill tube 134 and pivotably connected to leg 170 at pin 230, which extends through hole 183. Likewise, bracket member 204 is fixed to alignment drill tube 136 and is pivotably connected to leg 172 at pin 232, which extends through hole 185. Straight section 142 of handle member 114 is coupled to base 210. Preferably, a pin 234 extends through coaxial holes in base 210 and straight section 142. Thus, base 210 is held at a fixed distance from vertex 156 of handle 122.

Movement toward extended and retracted positions of alignment tubes 134, 136 is facilitated by pivotal connections at pins 130, 132. As handle 122 is squeezed, the position of actuation arm 116 is translated, and consequently the positions of alignment drill tubes 134, 136 are translated.

Figure 11:
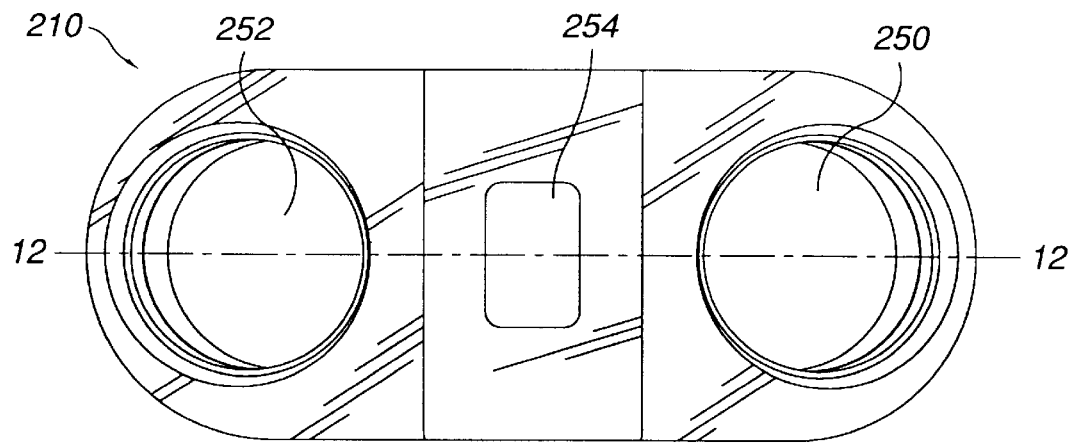
FIG. 11 is a side view of the base of the present invention.
Figure 12:
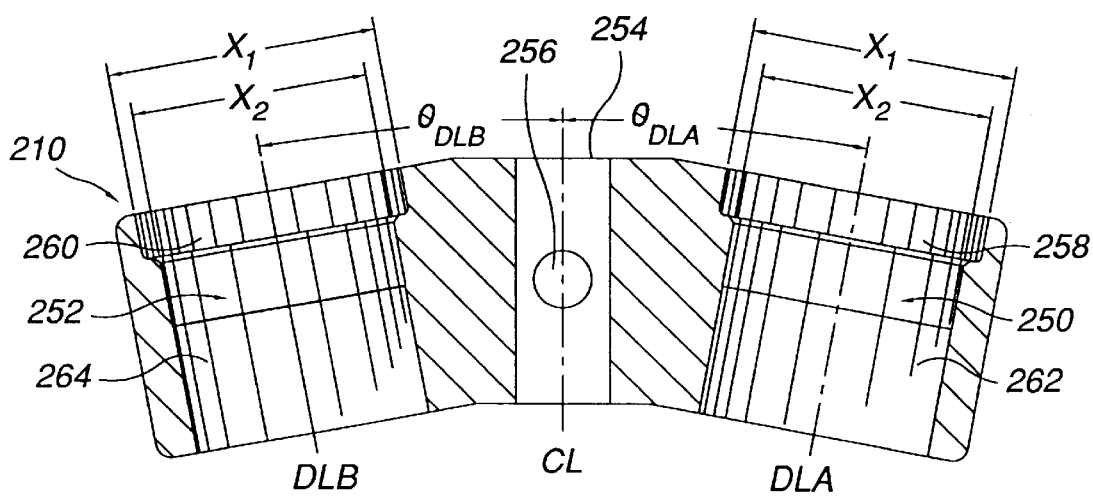
FIG. 12 is a cross-sectional view of the base of FIG. 11.

As shown in FIGS. 11–12, base 210 has retention holes 250, 252, as well as rectangular slot 254. Retention holes 250, 252 are configured and dimensioned to receive and hold therein bushings 206, 208 respectively. Slot 254 is configured and dimensioned to receive and hold therein straight section 142 of handle member 114. A pin hole 256 is provided through base 210 along the center plane to receive pin 234. Referring to FIGS. 2 and 12, base 210 is symmetrically disposed about the center plane. Furthermore, retention holes 250, 252 are disposed along lines DLA, DLB respectively. Thus, bushings 206, 208 held in retention holes 250, 252 are also aligned along lines DLA, DLB. Notably, FIG. 12 shows a partial cross-sectional view of base 210 taken along line 12—12 of FIG. 11. Retention holes 250, 252 have shoulder portions 258, 260 respectively with inner diameters $x_1$. Retention holes 250, 252 also have main portions 262, 264 with inner diameters $x_2$. As will be further discussed, because inner diameters $x_1$ are larger than inner diameters $x_2$, retention holes 250, 252 provide a secure means of retaining bushings 206, 208.

Figure 13:
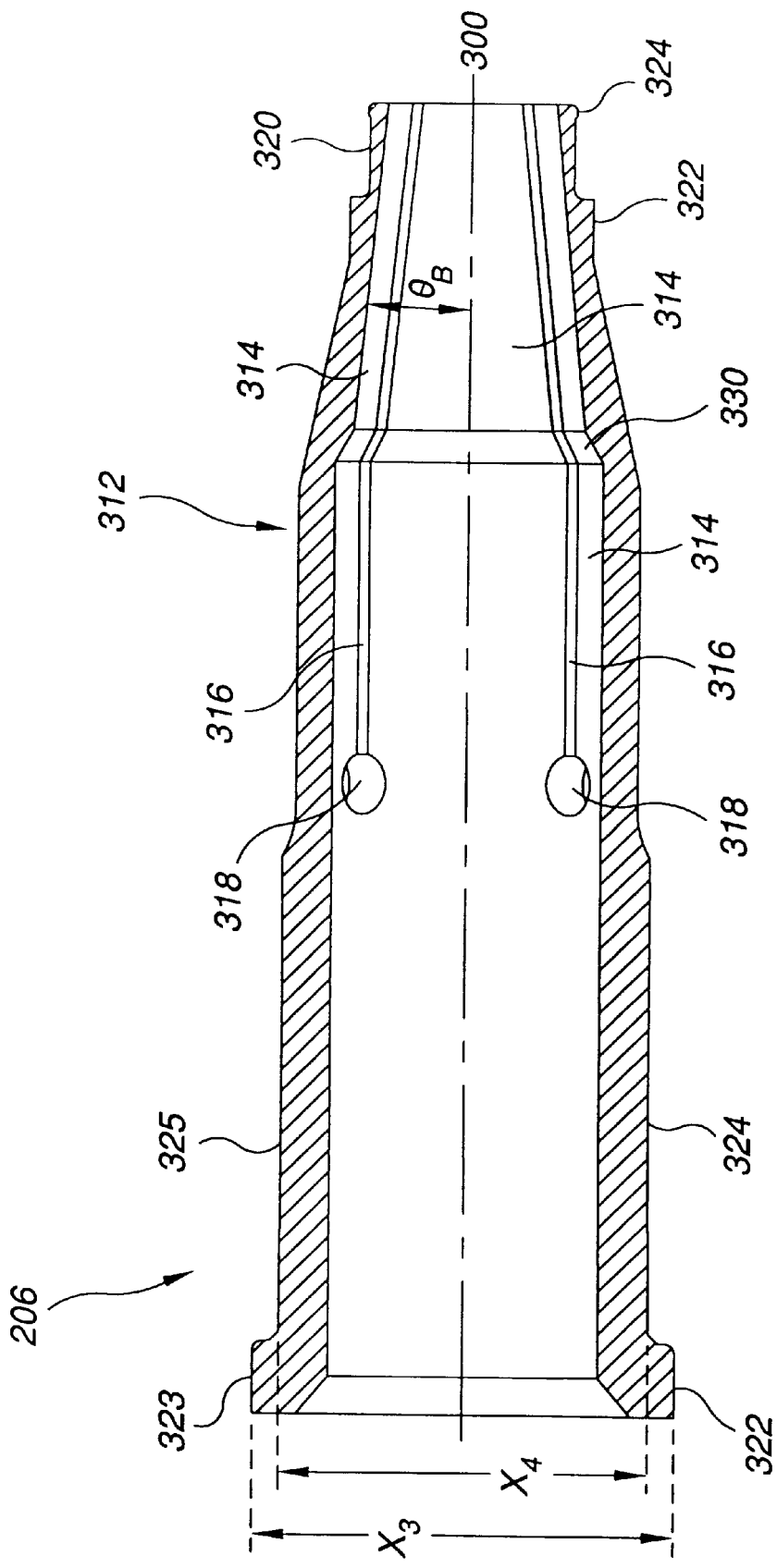
FIG. 13 is a cross-sectional view of a bushing in accordance with a preferred embodiment of the present invention.

Referring to FIG. 13, a bushing according to the preferred embodiment of the present invention is shown. For the purposes of describing this preferred bushing, FIG. 13 is directed only to exemplary bushing 206. However, it should be recognized that bushing 206 and bushing 208 have identical geometry, and thus the description of bushing 206 applies directly to the description of bushing 208. Bushing 206 coaxially receives alignment drill tube 134 about a central line 300. Notably, when bushing 206 is installed in retention hole 250, line 300 is colinear with line DLA. Preferably, bushing 206 is substantially symmetrical about line 300. The forward end 312 of bushing 206 is preferably comprised of longitudinally extending fingers 314. Individual fingers 314 are separated by slits 316 extending longitudinally between adjacent fingers 314. Slits 316 are shown, for example, in FIG. 13, may include a circular portion 318 that serves to help minimize stress concentration when fingers 314 are flexed. These fingers 314 are resiliently biased inwardly and naturally assume an inward disposition when in a relaxed state and when alignment drill tube 134 is in the retracted position. In the preferred embodiment, the inward bias of fingers 314 is selected to produce the desired friction, while allowing operation of handle 122 with only one hand. Alternative resiliency for fingers 314 may be chosen according to the purposes of other embodiments. At a frontmost portion of the expandable forward end 312 of bushing 206, the fingers 314 form a radially expandable circumferential neck 320, At the back end of and adjacent to neck 320 is a shoulder 322.

In the preferred embodiment, projections that form a radially expandable rim 324 are provided at the front end of and adjacent to neck 320. In alternate embodiments, no rim may be used. For example, in an embodiment without a rim, neck 320 may be tapered with the frontmost portion of neck 320 having a larger diameter than the portion of neck 320 adjacent shoulder 322. Thus, such a tapered neck may expand within a similarly tapered hole in a bone plate, to effectively provide firm alignment of the alignment drill tube. The several portions of bushing 206, i.e., the neck 320, the shoulder 322, and the rim 324, are preferably a single piece of material of unitary construction. In the contracted position shown in FIG. 13, neck 320 and rim 324 of bushing 206 are sized to fit freely through a fastener hole of similar geometry in a bone plate. Preferably, neck 320 together with rim 324 span a length that is slightly longer than the thickness of the fastener hole wall from the bone-side surface to the free-side surface of a locking bone plate. Thus, neck 320 can abut the wall of the locking bone plate fastener hole and rim 324 can abut the bone-side surface of the plate. In this manner, the drill guide assembly can be secured to the plate, restricting relative movement. In other alternate embodiments, fingers 314 need not include a shoulder, neck, and/or a rim. Instead, for example, a small pin may be used to secure the bushings to the plate.

Bushing 206 along with alignment drill tubes 134, 136, as described herein, are substantially similar to the collet, sleeve, and tissue protector illustrated and described in U.S. Pat. No. 5,851,207, the disclosure of which is hereby expressly incorporated by reference in its entirety.

Referring to FIG. 13, bushing 206 has a circumferential ridge 323 with an outer diameter $x_3$, and a region 325 has an outer diameter $x_4$. Bushing 206 is thus configured and dimensioned such that ridge 323 fits snugly within shoulder portion 258 of retention hole 250. Thus, outer diameter $x_3$ of ridge 323 is about the same size as inner diameter $x_1$ of shoulder portion 258. Similarly, region 325 fits snugly within main portion 262 of retention hole 250, with the outer diameter $x_4$ of region 325 about the same size as inner diameter $x_2$ of main portion 262. Bushing 206 may be permanently fixed to base 210, or it may be fastened thereto by other means.

Figure 14:
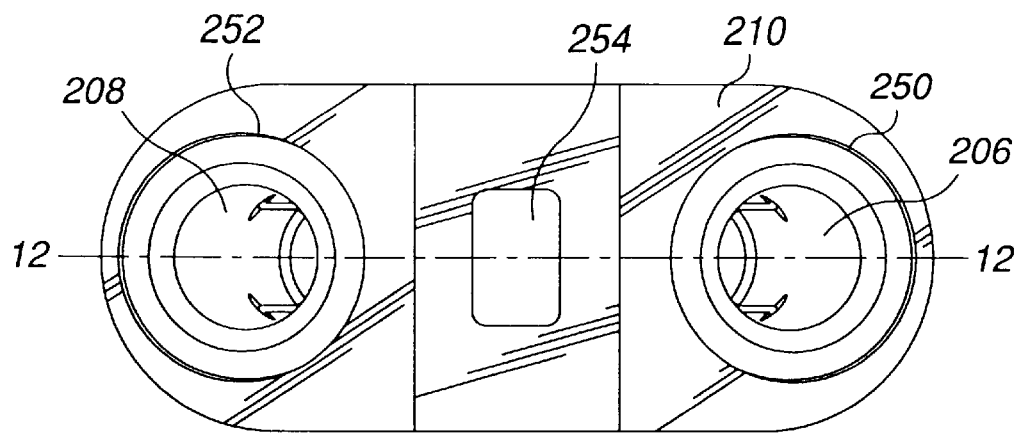
FIG. 14 is a side view of two bushings inserted within the base in accordance with a preferred embodiment of the present invention.
Figure 15:
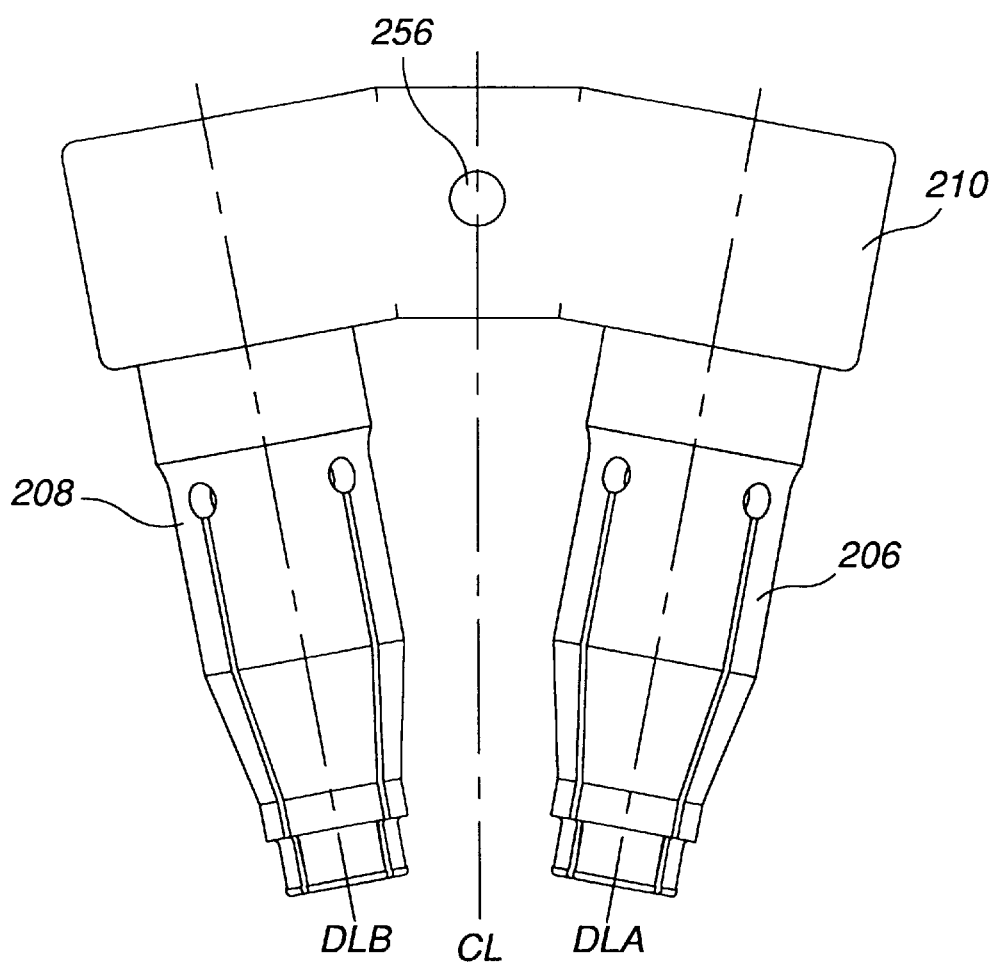
FIG. 15 is a top view of two bushings inserted within the base of FIG. 14.

As shown in FIGS. 14–15, bushings 206, 208 are coupled to base 210 within retention holes 250, 252 respectively. Because alignment drill tubes 134, 136 are received in bushings 206, 208 coaxially about lines DLA, DLB, the paths of surgical drill bits inserted in alignment drill tubes 134, 136 will converge forward of alignment device 110.

Figure 16:
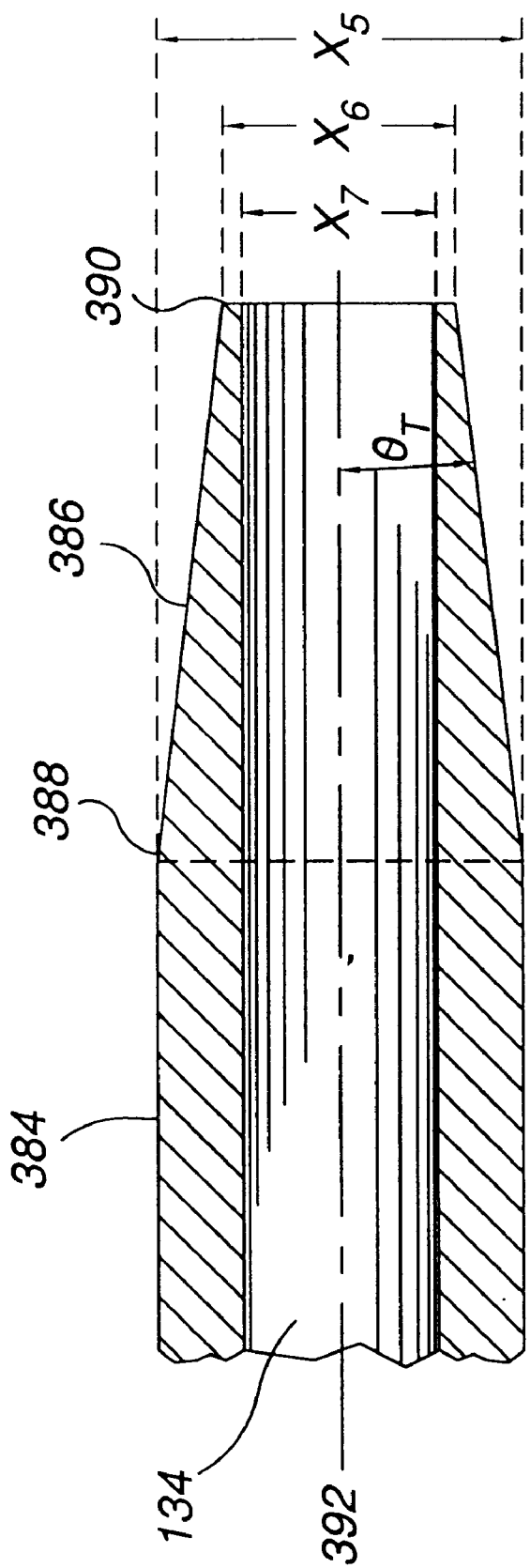
FIG. 16 is a partial cross-sectional view of the alignment drill tube in accordance with a preferred embodiment of the present invention.

Referring to FIG. 16, an alignment drill tube according to the preferred embodiment of the present invention is shown. For the purposes of describing this preferred alignment drill tube, FIG. 16 is directed only to exemplary alignment drill tube 134. However, it should be recognized that alignment drill tubes 134, 136 have identical geometry, and thus the description of alignment drill tube 134 applies directly to the description of alignment drill tube 136. In the preferred embodiment, alignment drill tube 134 is hollow with a cylindrical section 384 and a tapered, conical section 386 to facilitate movement of alignment drill tube 134 within bushing 206. Cylindrical section 384 has a diameter $x_5$, while conical section 386 tapers from a diameter $x_5$ at the transition 388 to a diameter $x_6$ at end 390. Preferably, inner diameter $x_7$ is constant along the length of alignment drill tube 134 as defined along center line 392.

Alignment tube 134 is aligned within bushing 206, such that center line 392 is colinear with line 300. Preferably, when bushing 206 is placed in a fastener hole of a bone plate, and actuation bar 116 is actuated such that the almost fully actuated position is reached (i.e. when grip 112 is separated by an angle $\theta_{ALI}$ from handle member 114), end 390 of alignment tube 134 is substantially coplanar with rim 324 of bushing 206.

Alignment drill tubes 134, 136 are configured and dimensioned to be slidably received within bushings 206, 208. Thus, the alignment drill tubes 134, 136 and bushings 206, 208 cooperate to permit drill guide assembly 100 to lock to a bone plate. The conical section 386 of each alignment drill tube 134, 136 cooperates with respective fingers 314 of each alignment tube 134, 136 to expand fingers 314 when the alignment drill tubes 134, 136 are moved into a locked position. Each conical section 386 of alignment drill tubes 134, 136 pushes outwardly against the inner surface of bushings 206, 208 respectively as alignment drill tubes 134, 136 are moved forward to expand the forward end 312 of each bushing 206, 208. In this embodiment, the conical section mates with and pushes against the inner surface of each bushing 206, 208 forward of circular portion 318 of slits 316 in fingers 314, to push the fingers 314 radially outward.

When the alignment drill tubes 134, 136 are in the unlocked position as shown in FIG. 9, the conical section 386 allows fingers 314 to return to a relaxed, contracted position. This allows bushings 206, 208 to be inserted and retracted from plate fastener holes. The inner surfaces of the bushings 206, 208 forward of steps 330 in bushings 206, 208 are preferably tapered at an angle $\theta_B$ to line 300 that is about 1° more than taper angle $\theta_T$ of conical sections 386, and preferably angle $\theta_B$ is about 4°. A desirable amount of movement of alignment drill tubes 134, 136 within bushings 206, 208 is thus provided to bias fingers 314 of bushings 206, 208 from a contracted position to an expanded position. Alternative taper angles of conical section 386 and inner surfaces of bushings 206, 208 may be chosen according to the purposes of other embodiments. In addition, a preferred, short travel of scissor grip 112 is required to expand and contract fingers 314 of bushings 206, 208.

Before and during locking bone plate implantation, the surgeon may insert the expandable forward ends 312 of bushings 206, 208, in particular neck 320 and rim 324, into fastener holes in a bone plate. By squeezing handle 122, the surgeon may grasp and manipulate the plate without an additional plate holder if he or she so desires. Preferably, friction between the forwardly moved conical section 386 of each alignment drill tube 134, 136 and the inner surface of fingers 314 especially at neck 320 and rim 324 retains the expandable forward end 312 of bushings 206, 208 in an expanded, locked position. Thus, when bushings 206, 208 are in the expanded, locked position in fastener holes of a plate placed against the cervical vertebrae, plate motion during the drilling operation can be minimized.

Alignment drill tubes 134, 136 preferably have a fixed orientation with respect to the center plane, such that the angular separation $\theta_{DLA}$ between drilling line DLA and the center plane is equal to the angular separation $\theta_{DLB}$ between drilling line DLB and the center plane. Angular separations $\theta_{DLA}$, $\theta_{DLB}$ are each between about 5 and 22°, preferably between 10° and 11°, and most preferably 10.5°. Advantageously, the fixed medial convergence of the drilling lines DLA, DLB makes the drilling and screw implantation process predictable, inasmuch as the risk of one screw hitting the other screw during implantation is significantly diminished. Furthermore, the insertion of the screws convergent toward the sagittal plane provides better fixation to the bone and concomitant resistance to screw backout. Drill tubes 134, 136 are preferably sized so that once the bone plate is properly positioned over the implantation site and bushings 206, 208 are locked to the plate, the insertion points of a surgical drill bit at the ends of drill tubes 134, 136, opposite ends 390, are located at a distance beyond the patient's body such that a spinning surgical drill bit will not laterally reach or harm surrounding tissues that the surgeon does not intend to drill.

Preferably, the surgical drill bits used with surgical drill guide assembly 100 are configured and dimensioned to drill holes of about 12, 14, or 16 mm in depth. Suitable drill bits typically have integral stops so that when the drill bits are used with alignment drill tubes of an established length, the holes produced by the drill bits will not be deeper than the intended depth using a given bit. The stops may be positioned to abut the upper surfaces at the ends of drill tubes 134, 136, opposite ends 390 respectively when drill bits have been inserted in the tubes to a particular depth.

Preferably, the surgical drill bits used with surgical drill guide assembly 100 are configured and dimensioned to drill holes of about 12, 14, or 16 mm in depth. Suitable drill bits typically have integral stops so that when the drill bits are used with alignment drill tubes of an established length, the holes produced by the drill bits will not be deeper than the intended depth using a given bit. The stops may be positioned to abut the ends of drill tubes 134, 136, opposite ends 390 respectively when drill bits have been inserted in the tubes to a particular depth.

Those skilled in the art will recognize that bushings 206, 208 may be configured and dimensioned to fit bone plate fastener holes with arcuate shapes other than circular. For example, bushings 206, 208 may be adapted to fit elliptical, hexagonal, star-shaped, or square fastener holes.

Preferably, the components of surgical drill guide assembly 100 are metallic, passivated, and electropolished. Most preferably, the components are formed of stainless steel, except for the springs which are formed of spring steel. Preferably, at least the handle member is forged, while the other components are machined, and the surgical drill guide assembly preferably has a matte finish so that the surfaces of the components do not reflect operating room light in such a manner as to distract the surgeon. Some components may be subjected to heat treatments so that the surfaces are work hardened. The surfaces are preferably burr-free. Thus, such a surface finish allows individual components to move with respect to each other in a smooth and non-binding fashion through each component's entire range of motion. Additionally, all pins and fasteners are preferably flush with the surfaces into which they are fixed.

The present invention also involves a method of drilling holes in cervical vertebra. A surgeon inserts the bushings of a surgical drill guide assembly into plate holes and squeezes the handle to slide the alignment drill tubes forward, expanding the bushings with the conical portions of the alignment drill tubes and locking the drill guide assembly to the plate. The surgeon then releasably locks the bushings to the plate by locking the alignment drill tubes and respective bushings in fixed relation to each other, thereby relieving the surgeon of the need to squeeze the handle. The surgeon aligns the surgical drill bit along the drilling axis defined through the center of the bore in the first alignment drill tube and inserts the drill bit in the tube. The surgeon then drills a first hole coaxial with the central axis of a first fastener hole in the plate. The surgeon then aligns the surgical drill bit along the drilling axis defined through the center of the bore in the second alignment drill tube and inserts the drill bit in the tube. The surgeon then drills a second hole coaxial with the central axis of a second fastener hole in the plate. He or she unlocks the bushings from the plate, opens the handle of the drill guide to contract the bushings from the fastener holes, and then freely and unfetteredly removes the drill guide assembly from the plate.

While the invention has been shown and described herein with reference to particular embodiments, it is to be understood that the various additions, substitutions, or modifications of form, structure, arrangement, proportions, materials, and components and otherwise, used in the practice of the invention and which are particularly adapted to specific environments and operative requirements, may be made to the described embodiments without departing from the spirit and scope of the present invention. For example, the surgical drill guide assembly may have alignment drill tubes that can be singly or together angulated in the cephalad/caudal or sagittal planes, thereby permitting a range of angles to be chosen for the holes to be drilled and further permitting a range of spacings of plate holes to be accommodated. Moreover, alignment drill tubes that are demountably attachable to the base may be provided so that a surgeon may select alignment drill tubes with holes that precisely accommodate a desired drill bit size. In addition, the drill guide assembly handle may include a grip that generally follows the contours of fingers that hold the grip. Furthermore, the drill guide assembly handle may include a handle member and grip with opposing and overlapping clamp tabs, the tabs each having teeth that are biased such that the tabs can be releasably locked with respect to each other when the teeth of one tab engage the teeth of the other tab. Thus, the separation distance between the handle member and grip may be fixed by a surgeon despite the biasing of assembly handle springs. The presently disclosed embodiments are therefore to be considered in all respects as illustrative and not restrictive, the scope of the invention being indicated by the appended claims, and not limited to the foregoing description.

What is claimed is:

1. A surgical drill guide assembly comprising:
   a pair of alignment drill tubes each configured to receive and guide a surgical drill bit;
   a pair of bushings configured to slidably receive the pair of alignment drill tubes along a fixed medial convergence, the bushings each having a radially expandable forward end configured to engage fastener holes in a bone plate;
   an actuation bar;
   a drill guide assembly handle coupled to the actuation bar;
   a base coupled to the drill guide assembly handle; and
   wherein the alignment drill tubes are pivotably connected to the actuation bar and the bushings are configured and dimensioned to expand within the bone plate fastener holes to releasably lock the bushings to the bone plate, such that movement of the actuation bar toward the base urges the drill tubes into the bushings for expansion of the forward ends thus locking the bushings within the fastener holes of the bone plate.

2. The surgical drill guide assembly of claim 1, wherein the radially expandable forward end comprises a plurality of finger portions.

3. The surgical drill guide assembly of claim 2, wherein the radially expandable forward end is circular.

4. The surgical drill guide assembly of claim 1, wherein the radially expandable forward end comprises a shoulder, a neck, and an outwardly projecting rim disposed forward of the neck.

5. The surgical drill guide assembly of claim 1, wherein each alignment drill tube has a drilling axis, and the drilling axes are coplanar and converge along a central plane forward of the radially expandable forward end of the bushings.

6. The surgical drill guide assembly of claim 5, wherein each alignment drill tube is oriented at an angle of between about 5 and 22° with respect to the central plane.

7. The surgical drill guide assembly of claim 6, further comprising a latch for releasably maintaining the actuation bar in an actuated position.

8. The surgical drill guide assembly of claim 1, wherein the expandable forward end of the bushing is circular shaped, and the fastener holes in the bone plate each have inner walls that define a circular shape, the expandable forward end being freely insertable and extractable from the bone plate fastener holes in a contracted position and engaging the fastener holes when in an expanded position.

9. The surgical drill guide assembly of claim 8, wherein the drill guide assembly handle is comprised of a grip pivotably connected to a handle member, the grip being resiliently biased away from the handle member by leaf springs.

10. The surgical drill guide assembly of claim 9, wherein in a first position, the leaf springs maintain the grip and handle member in a spaced relation, with the bushings in non-expanded configurations and the alignment drill tubes in retracted positions; and wherein application of a force to the grip and handle member counteracts the bias of the leaf springs and urges the grip and handle member to a second position while moving the actuation bar toward the base, and urging the alignment drill tubes into the bushings for expansion of the forward ends.

11. The surgical drill guide assembly of claim 8, wherein:
   the bone plate fastener holes each have a wall thickness defined as the distance between a free-side surface and a bone-side surface of the bone plate; and
   the radially expandable forward end of the bushing comprises a shoulder, a neck, and an outwardly projecting rim disposed forward of the neck;
   wherein the neck and rim together span a length that is slightly longer than the thickness of the bone plate fastener hole wall and the rim abuts the bone-side surface of the plate.

12. The combination of the drill guide assembly of claim 1 and a bone plate that includes at least two fastener holes.

* * * * *